(12) United States Patent
Kahn et al.

(10) Patent No.: US 7,842,075 B2
(45) Date of Patent: Nov. 30, 2010

(54) LASER PROBE FOR LIGHT THERAPY

(76) Inventors: Fred Kahn, 65 Harbour Square, Suite 1908, Toronto, Ontario (CA) M5J 1K6; Eli Hacco, 104 Fern Avenue, Toronto, Ontario (CA) M6R 1K3; Mark Anthony Peter Slonchka, 30 Allanhurst Crescent, Brampton, Ontario (CA) L6P 1C8

( * ) Notice: Subject to any disclaimer, the term of this patent is extended or adjusted under 35 U.S.C. 154(b) by 0 days.

(21) Appl. No.: 11/785,194

(22) Filed: Apr. 16, 2007

(65) Prior Publication Data

US 2007/0255358 A1 Nov. 1, 2007

(51) Int. Cl.
*A61N 5/067* (2006.01)

(52) U.S. Cl. .............................. 607/88; 607/89; 606/10

(58) Field of Classification Search ............. 607/88–92; 606/4–12; 372/9
See application file for complete search history.

(56) References Cited

U.S. PATENT DOCUMENTS

| 6,733,493 | B2 * | 5/2004 | Gruzdev et al. | 606/9 |
| 7,217,267 | B2 * | 5/2007 | Jay | 606/18 |
| 7,275,931 | B2 * | 10/2007 | Katsuda et al. | 433/29 |
| 7,291,140 | B2 * | 11/2007 | MacFarland et al. | 606/9 |

* cited by examiner

*Primary Examiner*—Ahmed M Farah

(57) ABSTRACT

A laser light therapy treatment probe, having an internal control circuit, and a manual control, a connection to a power supply, and a laser light treatment source, whereby the laser light treatment probe, and may be plugged into a supply of electrical power, and having an on/off switch connected between the control circuit and the laser light treatment source, and wherein the laser light source is switched on, for example by pressing the probe against the skin.

4 Claims, 1 Drawing Sheet

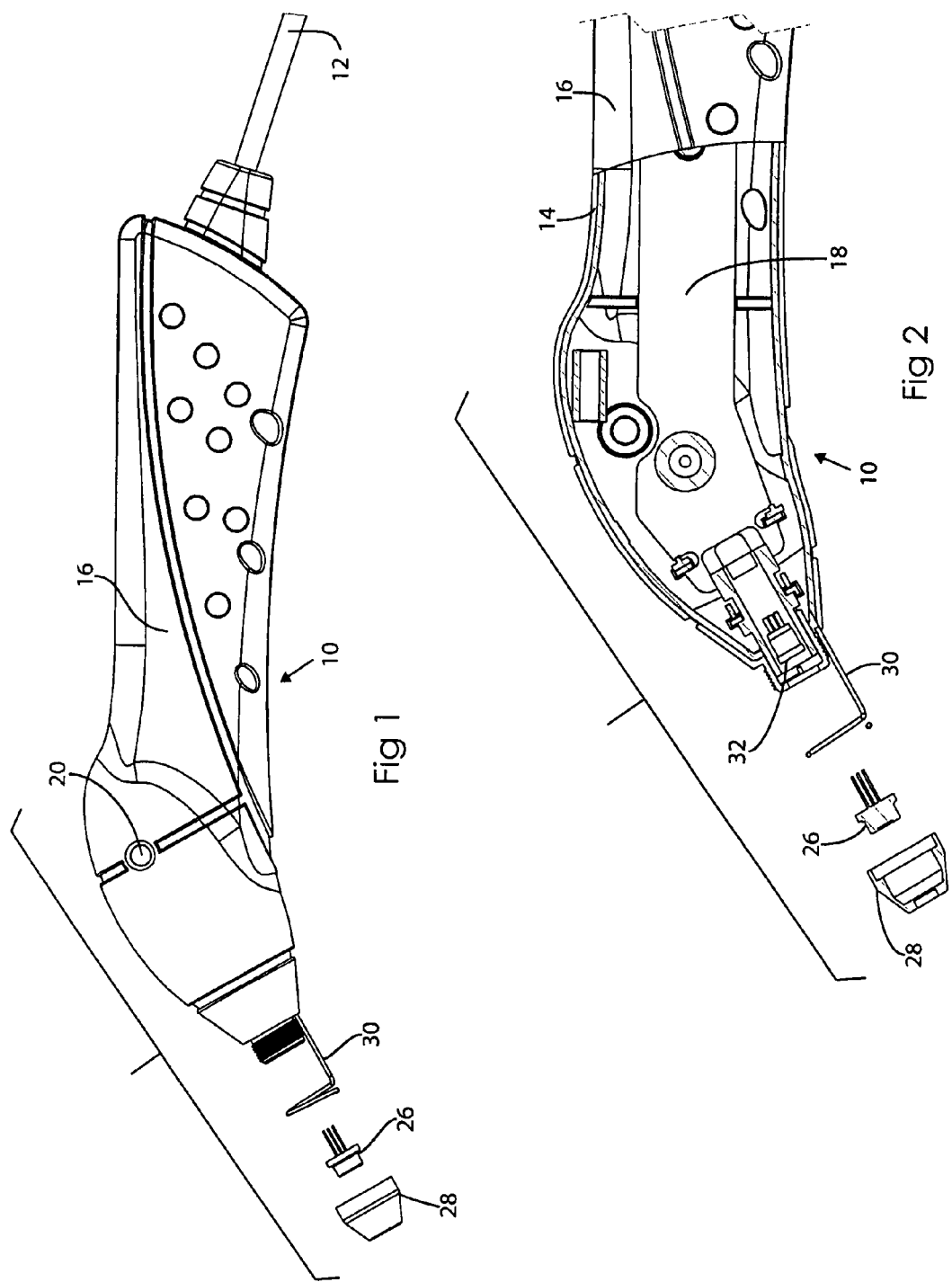

LASER PROBE FOR LIGHT THERAPY

FIELD OF THE INVENTION

The invention relates to the field of light treatment therapy, and equipment for such therapy.

BACKGROUND OF THE INVENTION

Light treatment of patients for various conditions is becoming well known. Light treatment of injuries such as sport injuries, sprains and the like, light treatment of chronic conditions such as arthritis, sciatica and various related conditions, and treatment of chronic slow healing wounds or sores, are all well known.

The principle of all these light treatments is the application of low intensity light radiating in the area of the patient's condition. It is found that in order to be effective, the light source should be close in contact with the skin. One such light source may comprise an array or panel of low intensity light emitting diodes, or in some cases low level laser. It is also found that the treatment becomes more effective if it is applied over longer periods of time. In some cases the light sources are left in contact with the skin for thirty to sixty minutes. In the case of low level laser, the light source is often a single light source, and it may be applied for a few minutes at each of many locations in the area of the body to be treated. The deep penetration of the light rays into the tissues, produces the healing results experienced.

In the past, treatment of patients with light therapy has involved as a partial component of the treatment protocol, the use of a laser light treatment head or probe. This was connected to a computer. The computer contained programs for programming the operation of the light laser treatment probe and would regulate the therapy. It would also record the length of therapy and the location and compile records of treatment. The probe was held in the hand of a therapist who directed the probe onto various locations in the area of the body for treatment.

While the system had advantages in the sense of capturing information immediately, it had the disadvantage that the probe, and thus therapist and the patient were, as it were, all tied to the computer. Consequently, the treatment of a single patient would involve a laser light treatment probe, a therapist, and a dedicated computer. This greatly increased the cost of the laser light therapy treatment. In addition, it reduced the ability of a clinic to service a number of patients simultaneously. As a result, while the investment in any given clinic, for a given number of patents on a per patient basis was high, the return on investment was low, since it was possible to treat only a limited number of patients at one time.

Clearly, it is desirable to provide a system in which the laser light probe therapy can be provided to a variety of different patients in a given clinic, without the necessity for providing a connection between each treatment probe and a computer.

BRIEF SUMMARY OF THE INVENTION

A laser light therapy treatment probe, having an internal control circuit, and a manual control, a connection to a power supply, and a laser light treatment source, whereby the laser light treatment probe, and may be plugged into a supply of electrical power, and having a contact sensitive on/off switch connected between the control circuit and the laser light treatment source, whereby the laser light treatment source is off, when there is no skin contact, and wherein the laser light source is on when it is in contact with the skin, for example by pressing the probe against the skin.

Preferably the probe has a two part housing, formed by mating left and right side portions.

There is a light source mounted in a socket. When the socket contacts the skin the socket completes the circuit and activates the light source.

Preferably the housing forms a handle by which the probe may be grasped and operated with one hand, and a power cord extends from the handle for connection to power.

Preferably there is a circuit board within the housing operable to provide power to the light source for emitting light for treatment.

Preferably there is an on/off button on one side of one housing part which may be operated to switch the probe on or off.

IN THE DRAWINGS

FIG. 1 is a perspective illustration showing a typical laser light treatment probe illustrating the invention, and a connection to a power supply; and FIG. 2 is an exploded side elevation of the probe.

DESCRIPTION OF A SPECIFIC EMBODIMENT

Referring to FIG. 1, it will be seen that the invention is there illustration in the form of a laser light treatment probe (10), having a cord (12) adapted to be connected to a power supply.

The laser light treatment probe is of the type that incorporates a single laser light treatment source, in this case typically a class 3 laser, or other forms of lighting source including laser light may be provided.

The probe is illustrated in more detail in FIG. 2, and will be seen to consist of a right side panel (14) and left side panel (16), which may be mated together to form an enclosure. Typically the enclosure will be sized to fit conveniently in the hand of an operator, and may be about the size of a flashlight, substantially as shown, this being merely one particularly convenient example. Other shapes will suggest themselves to persons skilled in the art for various reasons, and the invention is not restricted to such shape. Within the side panels, there is a circuit board (18), on which is mounted a miniature CPU, and various electronic components such as are well known in the art. Alternatively there could be a mode control, for connecting to a variety of different mode programs within the device. Such systems are well known in the art and require no special description and will typically provide various functions such as an on off, a timer control, and a power control for adjusting the power supply, and intensity of the light.

The button(s) extend through suitable openings (22) in a side panel of the probe (10) for easy access. The invention is not specifically limited to any unique sequence of functions, and various different functions may be incorporated, without departing from the scope of the invention.

The probe is provided with an electrical power cord (12) at one end. At the other end, the probe is provided with a treatment light assembly, comprising a treatment light socket (24), a light source, in this case a low level laser light source (26), and a protective cap (28). A spring wire connection (30) is provided, for connecting with the protective cap. The light source is provide with a plurality of contacts (34), which contact internal circuits (not shown) for supplying power from the circuit board to the light source.

The socket (24) is of generally cylindrical shape, and is received within a recess (32), formed in the opposite left and right side panels. The protective cap (28) is formed of metal, and is connected by connection (30) to control circuits on the board (18). The cap (28) when contacted on the skin, functions like the buttons of an elevator, for example. The skin contact is sensed by the control circuits on the board (18) and switches on power to the light source (26). The purpose of this is to ensure that unless and until the protective cap (28) is pressed on the skin, the light source will not be activated.

When the protective cap (28) is pressed on the skin, the control circuits will activate the light source (26). Treatment will then be applied to that area of the body to which the probe is directed and applied. The moment the probe is lifted off the skin, contact to the light source is then broken, and no light will be emitted.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A laser light therapy treatment probe, and comprising;
a housing adapted to be hand held;
an internal control circuit, within said housing;
a laser light treatment source supported by said housing and connected to said control circuit;
a socket for said laser light treatment source connected to said control circuit;
a protective cap having a contact sensitive surface on said socket;
an on/off switch connected between the control circuit and the protective cap for the laser light treatment source, whereby the laser light treatment source is off, when there is no contact with the skin, and wherein the contact sensitive surface of said protective cap is configured/adapted to turn the treatment laser source on when it contacts the skin, and to turn off the laser source when it is not in contact with the skin; and,
a moveable and retractable spring wire connection connecting the protective cap with said control circuit.

2. A laser light therapy treatment probe as claimed in claim 1 and having a two part housing, formed by left and right side portions.

3. A laser light therapy treatment probe as claimed in claim 1 wherein said housing forms a handle by which the probe may be grasped and operated with one hand, and a power cord extends from the handle for connection to power.

4. A laser light therapy treatment probe as claimed in claim 3 wherein said control circuit is mounted on a board within said housing and is operable to provide power to the light source for emitting light for treatment.

* * * * *